United States Patent [19]
Heath et al.

[11] Patent Number: 5,302,129
[45] Date of Patent: Apr. 12, 1994

[54] ENDODONTIC PROCEDURE AND INSTRUMENT

[76] Inventors: Derek E. Heath, 1917 Sherwood Dr., Johnson City, Tenn. 37604; Jerry A. Mooneyhan, 711 N. Mountainview Cir., Johnson City, Tenn. 37601

[21] Appl. No.: 794,069
[22] Filed: Nov. 19, 1991
[51] Int. Cl.$^5$ ............................. A61C 5/02; A61G 5/02
[52] U.S. Cl. ................................. 433/224; 433/81; 433/102
[58] Field of Search .................... 433/81, 102, 224

[56] References Cited

U.S. PATENT DOCUMENTS

| | | | |
|---|---|---|---|
| 4,299,571 | 11/1981 | McSpadden | 433/102 |
| 4,332,561 | 6/1982 | McSpadden | 433/102 |
| 4,353,698 | 10/1982 | McSpadden | 433/164 |
| 4,457,710 | 7/1984 | McSpadden | 433/81 |
| 4,758,156 | 7/1988 | Johnson | 433/81 |
| 4,871,312 | 10/1989 | Heath | 433/164 |
| 4,894,011 | 1/1990 | Johnson | 433/224 |
| 4,934,934 | 6/1990 | Arpaio, Jr. et al. | 433/102 |
| 5,067,900 | 11/1991 | McSpadden | 433/224 X |
| 5,083,923 | 1/1992 | McSpadden | 433/224 |
| 5,089,183 | 2/1992 | Johnson | 264/16 |
| 5,098,298 | 3/1992 | Johnson | 433/224 |
| 5,118,297 | 6/1992 | Johnson | 433/224 |

OTHER PUBLICATIONS

Oral Surg., "The thermomechanical properties of gutta-percha", Jun., 1974, vol. 37, No. 6, pp. 954-961.

*Primary Examiner*—Gene Mancene
*Assistant Examiner*—Nicholas D. Lucchesi
*Attorney, Agent, or Firm*—Bell, Seltzer, Park & Gibson

[57] ABSTRACT

An endodontic procedure is disclosed which involves extirpating a root canal of a tooth, and then inserting a machine driven compactor which is coated with alpha phase gutta percha into the extirpated canal. The compactor is then rotated at a relatively high speed and so that the alpha phase gutta percha is plasticized solely by the frictional heat generated by the rotating compactor. The plasticized gutta percha is thrown radially outwardly, and pushed downwardly, so as to fill all of the voids of the canal, and the compactor is then withdrawn and the gutta percha cools and solidifies. A crown may be then fitted to the tooth above the gutta percha in the conventional manner.

13 Claims, 2 Drawing Sheets

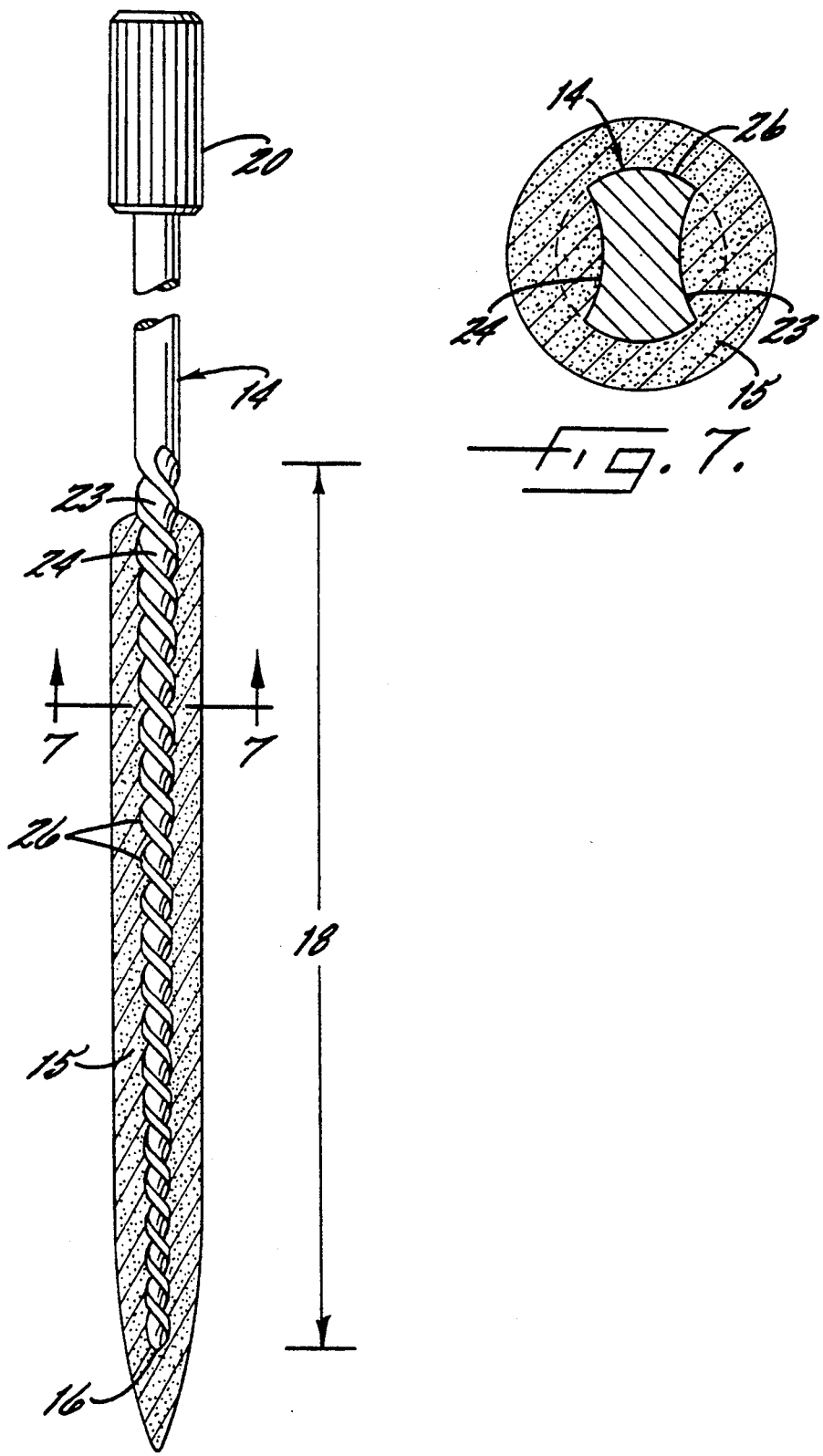

ENDODONTIC PROCEDURE AND INSTRUMENT

BACKGROUND OF THE INVENTION

The present invention relates generally to the field of endodontics, and more particularly to a method of applying a filler material in an endodontically prepared root canal.

Root canal therapy is a well-known procedure wherein the crown of a diseased tooth is opened so as to permit the canal to be cleaned and then filled. More particularly, a series of very delicate, flexible, finger-held instruments or files are used to extirpate or clean out and shape the root canal, and each file is manually rotated and reciprocated in the canal by the dentist. Files of increasingly larger diameter are used in sequence, to achieve the desired cleaning and shaping. When the canal is thus prepared, it is obturated or solidly filled with a filling material, which typically comprises a waxy, rubbery compound known as gutta percha.

In the traditional method of obturating a root canal, strand-like pieces of gutta percha, commonly referred to as "points", are inserted into the extirpated root canal. The points are then physically compacted by a compactor, which may be heated, and which is manipulated into contact with the points to soften and compact the material into the canal. This is a time consuming procedure, and it is difficult to insure that all portions of the canal are filled.

The Thermafil ™ compactor as sold by Tulsa Dental Products, consists of a compactor according to U.S. Pat. No. 4,871,312, with a manually engagable handle at one end. The opposite or distal end of the compactor is coated with a layer of alpha phase gutta percha. As hereinafter further described, alpha phase gutta percha has a somewhat different crystalline structure as compared to the more conventional beta phase, and alpha phase requires less heat to become plasticized than does beta phase.

To fabricate the Thermafil ™ compactor, conventional beta phase gutta percha is placed in a cavity in a mold, and the mold is heated under conditions of controlled heat and time to plasticize the gutta percha, which also serves to convert the gutta percha to alpha phase. The distal end of the compactor is inserted into the gutta percha in the cavity, and upon cooling, the gutta percha solidifies about the distal end. When ready for use, the dentist heats the gutta percha by means of a separate heat source, such as an open flame, until the gutta percha again plasticizes. The compactor is then inserted into the root canal and manipulated by hand to cause the gutta percha to fill the canal.

In the above procedure, it is difficult for the dentist to control the application of the external heat, and if the gutta percha becomes too hot, it will unduly shrink upon cooling and voids will be formed in the canal, causing leakage.

U.S. Pat. Nos. 4,894,011 and 4,758,156 to Johnson disclose an obturating procedure which includes a carrier having a manual handle and a shaft with a reduced diameter portion which is designed to fail when a certain level of torque is applied. Gutta percha is molded to the carrier, and in preparation for use, the gutta percha is heated by an external source to a temperature at which the surface becomes "glossy". The heated instrument is then inserted into the root canal, and the handle is rotated until torsional failure occurs. Thus the distal end portion of the shaft remains in the canal.

The procedure of the Johnson patents involves the same limitations noted above with regard to the difficulty of controlling the temperature to which the gutta percha is heated by the external source, and the resulting problems of shrinkage and voids in the canal.

U.S. Pat. No. 4,457,710 to Dr. John McSpadden discloses a procedure for obturating extirpated root canals wherein a gutta percha point is placed in the canal. A compactor having downwardly facing shoulders is then inserted in the canal and rotated at a speed of about 6,000 rpm or less, to thereby mechanically work the gutta percha and generate frictional heat which plasticizes the material. The compactor is then withdrawn longitudinally, with the shoulders of the compactor forcing the plasticized gutta percha downwardly and laterally.

A disadvantage of the procedure described in the cited McSpadden patent is the fact that the diameter of the compactor must closely approximate the diameter of the root canal, in order to insure that sufficient frictional heat is developed to plasticize the gutta percha, which has a relatively high melting point. More particularly, the gutta percha must be forced against the wall of the canal to cause enough friction to plasticize it, and a large diameter compactor is needed for this purpose. The use of a compactor of large diameter in turn causes problems, in that it does not have the ability to readily extend through the curves which are common in root canals. Also, they tend to extrude the gutta percha through the apex of the canal.

Dr. McSpadden has recently suggested a new procedure wherein gutta percha is placed in a tube which is supplied to the dentist. In use, the dentist heats the tube using an external heat source, and the compactor is then inserted into the tube to coat its distal end. The compactor with the heated gutta percha coating is then immediately inserted in the canal, together with an additional point of cold gutta percha, and the instrument is machine rotated at a relatively slow speed of about 2,000 rpm. The additional point of gutta percha is used to avoid an excessive amount of heated gutta percha with the attendant risk of shrinkage and voids. Also, the relatively slow speed is employed so as to avoid plasticizing the solid additional point, again to avoid the risk of overheating and shrinkage. This is seen to be a rather cumbersome procedure for the dentist, and there is a risk that the gutta percha in the tube may be overheated, causing its deterioration.

It is accordingly and object of the present invention to provide a method of applying gutta percha in an endodontically prepared root canal, and which avoids the above noted limitations and disadvantages of the prior art techniques.

It is a more particular object of the present invention to provide a method of the described type which utilizes only the frictional heat generated by the rotation of the compactor to plasticize the gutta percha, and which thereby avoids the need to apply external heat to the gutta percha immediately before the instrument is inserted into the canal.

It is a further object of the present invention to provide a method of the described type which permits the use of a compactor of relatively small diameter which serves to minimize the risk of damage by contact of the compactor with the walls of the canal.

It is still another object of the present invention to provide a novel endodontic compactor for use in carrying out the method of the present invention.

SUMMARY OF THE INVENTION

The above and other objects and advantages of the present invention are achieved in the embodiments illustrated herein by the provision of a method of applying a filler material in an endodontically prepared root canal which comprises the steps of providing an endodontic compactor having an elongate shank portion. The shank portion terminates in a pilot end, and preferably, at least one helical flute is formed in the shank portion along a working length of the shank portion adjacent the pilot end. Also, the flute is positioned so as to form helical lands on the periphery of the working length, with the lands extending between axially adjacent flute segments.

A quantity of gutta percha is heated in a mold for a predetermined time and at a predetermined temperature and so as to convert the crystalline structure from beta phase to alpha phase. The shank portion of the endodontic compactor is then inserted into the heated gutta percha in the mold, and the gutta percha is allowed to cool and solidify and form a coating about the shank portion. The coated compactor is then removed from the mold.

The above steps are normally conducted under controlled conditions in a manufacturing facility, and the coated compactor is then shipped to the endodontist. In performing the root canal therapy procedure, the endodontist extirpates the root canal by a conventional process, and the coated shank portion of the endodontic compactor is then inserted into the prepared root canal. The compactor is then rotated at a speed sufficient to plasticize the gutta percha solely from the frictional heat generated by the rotation of the compactor, and the compactor is then withdrawn from the canal and so as to leave the plasticized gutta percha therein. The gutta percha thereafter cools and hardens to form a solid filler in the canal.

In the preferred embodiment, the root canal is initially extirpated by serially inserting a plurality of files in the canal and manipulating each file in the canal, and with the files being of progressively increasing diameter. The endodontic compactor which is coated with gutta percha in the manner described above has a diameter less than the diameter of the largest file employed in the extirpating step. A compactor of such small diameter will inherently produce less frictional heat during rotation than would a compactor of larger diameter, but this smaller amount of heat has been found to be able to plasticize the alpha phase gutta percha without the need for an external heat source. Also, the presence of the helical lands on the periphery of the working length of the compactor is believed to facilitate the frictional heating, since the lands provide a relatively broad area of surface contact between the rotating compactor and the gutta percha. Further, the fact that a small diameter compactor may be used is significant in that its smaller diameter permits it to pass through any curves of the root canal, and there is less tendency to extrude the gutta percha through the apex of the canal. Also, a smaller diameter compactor minimizes the risk of damage by contacting the walls of the canal. In practice, it has been found that a compactor having a diameter which is at least about 0.004 inches (or about 2 standard sizes) less than the diameter of the last file used, is suitable.

The present invention has the further advantage that since the frictional heat alone is used to plasticize the alpha phase gutta percha, all external heat sources may be eliminated, which reduces the risk of overheating and the attendant problem of deterioration of the gutta percha and undue shrinkage in the root canal. In this regard, the frictional heat generated in the process of the present invention does not appear to present a risk of overheating, since it is believed that the gutta percha is thrown radially away from the rotating compactor as soon as it is plasticized, and thus it is not subjected to undue heat.

BRIEF DESCRIPTION OF THE DRAWINGS

Some of the objects and advantages of the present invention having been stated, others will appear as the description proceeds, when taken in conjunction with the accompanying drawings, in which FIGS. 1 and 2 schematically illustrate the initial steps of the present invention, and wherein a quantity of gutta percha is heated in a mold and the shank portion of an endodontic compactor is then inserted into the heated gutta percha in the mold;

FIG. 6 is an enlarged, partially sectioned view of the coated compactor of the present invention; and FIG. 7 is a sectional view taken substantially along the line 7—7 of FIG. 6.

DETAILED DESCRIPTION OF THE PREFERRED EMBODIMENT

Figure 1:
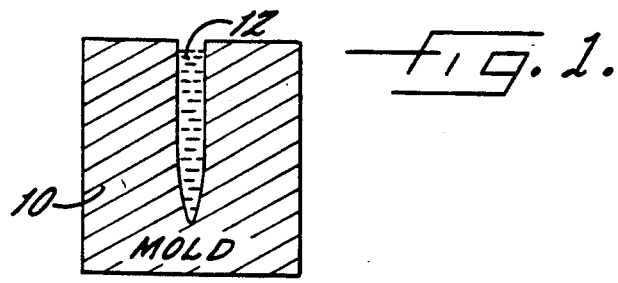
Figure 2:
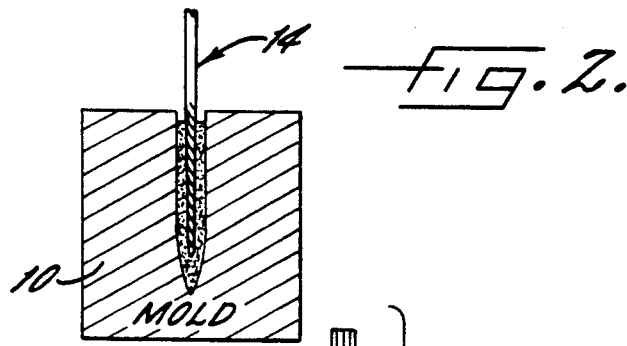

FIG. 1 schematically illustrates an initial step of the present invention and which involves filling a mold 10 with conventional beta phase gutta percha 12, and then heating the gutta percha under controlled temperature and time conditions. In this regard, gutta percha is commonly supplied in the form of beta phase, but it is recognized in the art that upon heating the beta phase gutta percha to a controlled temperature of about 275 degrees F. and for a controlled time of about seven hours, the crystalline structure is changed from beta phase to so called alpha phase. It is also recognized in the art that alpha phase gutta percha may be plasticized with less heat than is the case with beta phase. A more detailed discussion of the different phases of gutta percha may be obtained from the article entitled "The Thermo Mechanical Properties of Gutta Percha", *Oral Surgery*, Volume 37, No. 6, June 1974, pages 954–961.

Figure 3:
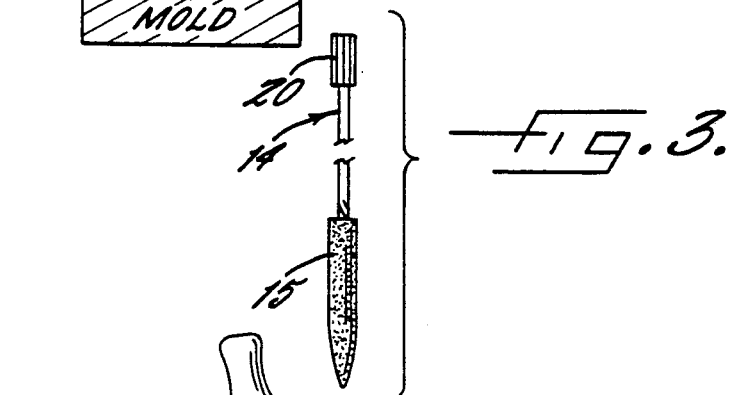
FIG. 3 is a side elevation view of the resulting coated compactor.

While the gutta percha 12 is still plasticized in the mold 10, the shank portion of an endodontic compactor 14 is inserted into the gutta percha, and the gutta percha is allowed to cool and solidify about the shank portion. The compactor 14 is then removed from the mold, as seen in FIG. 3, and so that the compactor 14 has a coating 15 of the alpha phase gutta percha.

The compactor 14 is preferably of a construction illustrated in U.S. Pat. No. 4,871,312 to Derek Heath, the disclosure of which is expressly incorporated herein by reference. As also illustrated in FIG. 6, the compactor 14 comprises a shank portion terminating at a pilot end 16, and includes a working length 18 adjacent the pilot end. The working length 18 may be cylindrical, but preferably, it is tapered toward the pilot end at an included angle of between about ½ and 4 degrees, as best seen in FIG. 6.

A coupling 20 of generally conventional design is mounted to the shank portion at the end thereof opposite the pilot end 16 for releasably connecting the compactor to the chuck 21 (FIG. 5) of a conventional machine driven handpiece. A pair of continuous helical flutes 23, 24 are formed in the working length 18 of the shank portion and so as to form a helical land 26 at the periphery of the working length and which extends axially between adjacent flute segments. The helical land thus lies along an arc of a circle when viewed in transverse cross section, i.e. as seen in FIG. 7. Preferably, the width of the land 26 is at least about 0.0004 inches, and it preferably has a width which is equal to at least 15 percent of the pitch of the helical flutes when viewed in longitudinal cross section. The "pitch" as defined herein is the distance between corresponding points of adjacent flute segments, and thus if two helical flutes are present as illustrated, the "pitch" is equal to ½ the actual pitch of one of the flutes. The flutes 23, 24 preferably have a left handed orientation, so that upon rotation in the clockwise direction, which is the industry standard, the gutta percha will tend to be pushed downwardly toward the pilot end 16.

The above steps of the method of the present invention are typically carried out at a manufacturing facility, where close temperature and time tolerances may be maintained. The coated compactor 14 is then shipped from the factory to the endodontist for use.

Figure 4:
FIG. 4 is a schematic representation of the step of extirpating the root canal with a series of manually manipulated files.

During the root canal therapy as performed by the endodontist, standard procedures are followed for opening the crown, and then extirpating the canal by employing a series of finger held files 28 as schematically illustrated in FIG. 4. The files 28 are mutually rotated and reciprocated in the canal, and files of progressively increasing diameter are used in sequence to achieve the desired cleaning and shaping of the canal. In this regard, such files are conventionally sold in standard sizes, which vary in diameter by about 0.002 inches between sizes. A suitable file of this type is further illustrated in U.S. Pat. No. 4,934,934 to Arpaio and Heath, and in copending U.S. application Ser. No. 07/679,628 filed Apr. 3, 1991.

Figure 5:
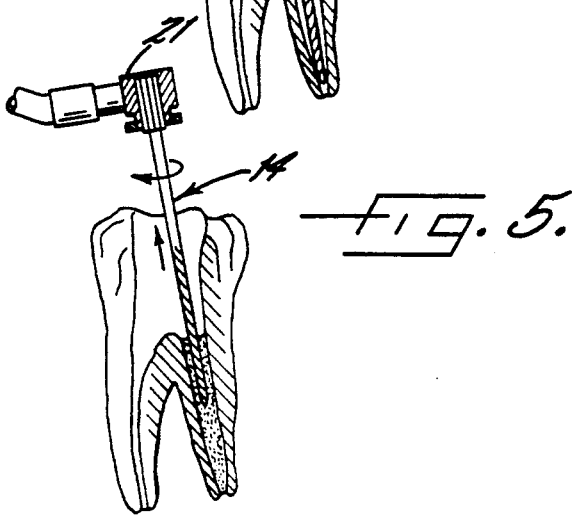
FIG. 5 illustrates the subsequent step of positioning the coated compactor in the extirpated root canal and machine rotating the compactor at high speed.

When the extirpation process is completed, a coated compactor 14 as seen in FIGS. 3 and 6 is selected. Preferably, a compactor of two sizes smaller than the last, i.e. largest, file used in the extirpation process is selected, so that the shaft portion of the compactor will have a diameter of about 0.004 inches less than that of the last file. The selected compactor is then connected to a machine driven handpiece as seen in FIG. 5, and the coated shank portion is inserted into the extirpated canal. The compactor is then machine rotated at a relatively high speed, preferably at least about 5,000 rpm, and the frictional heat of the rotation of the compactor is sufficient to quickly plasticize the alpha phase gutta percha. As the gutta percha becomes plasticized, it is thrown radially outwardly, and forced downwardly by the flutes 23, 24 of the rotating compactor, so as to fill all of the voids of the canal. The compactor is then withdrawn, and the gutta percha cools and solidifies in the canal. As final steps, the endodontist fills the area above the gutta percha with cement, and fits a crown to the tooth in the conventional manner.

In the drawings and specification, there has been set forth a preferred embodiment of the invention, and although specific terms are employed, they are used in a generic and descriptive sense only and not for purposes of limitation.

That which is claimed is:

1. A method of applying a filler material in an endodontically prepared root canal and comprising the steps of providing an endodontic compactor having an elongate shank portion, heating a quantity of gutta percha having a beta phase crystalline structure, and including heating the gutta percha in a mold for a predetermined time and at a predetermined temperature and so as to convert the crystalline structure from beta phase to alpha phase, inserting the shank portion of the endodontic compactor into the heated gutta percha in the mold and then allowing the same to cool and solidify and form a coating about the shank portion, positioning the coated shank portion of the endodontic compactor into the prepared root canal and then rotting the compactor at a speed sufficient to plasticize the gutta percha solely from the frictional heat generated by the rotation of the compactor, and then withdrawing the compactor from the canal and so as to leave the plasticized gutta percha therein, and such that the gutta percha then cools and hardens to form a solid filler in the canal.

2. The method as defined in claim 1 wherein said elongate shank portion terminates in a pilot end, with at least one helical flute formed in said shank portion along a length of said shank portion adjacent said pilot end, and with a helical land at the periphery of the shank portion and extending between axially adjacent flute segments.

3. The method as defined in claim 2 wherein with width of said helical land is at least about 15% of the pitch of said at least one helical flute.

4. The method as defined in claim 3 wherein said helical land lies along an arc of a circle when viewed in transverse cross section.

5. The method as defined in claim 4 wherein said compactor further comprises a coupling mounted at the end opposite said pilot end for releasably connecting the compactor to the chunk of a machine driven handpiece.

6. The method as defined in claim 1 wherein the step of rotating the compactor includes rotating the same at a speed of at least about 5000 rpm.

7. An endodontic procedure comprising the steps of extirpating a root canal and including serially inserting a plurality of files in the canal and manipulating each file in the canal, and with the files being of progressively increasing diameter, providing an endodontic compactor having an elongate shank portion of a diameter which is less than the diameter of the largest file employed in the extirpating step, heating a quantity of gutta percha having a beta phase cyrstalline structure, and including heating the gutta percha in a mold for a predetermined time and at a predetermined temperature and so as to convert the crystalline structure from beta phase to alpha phase, inserting the shank portion of the endodontic compactor into the heated gutta percha in the mod and then allowing the same to cool and solidify and form a coating about the shank portion, positioning the coated shank portion of the endodontic compactor into the extirpated root canal and then rotating the compactor at a speed sufficient to plasticize the gutta percha solely from the frictional heat generated by the rotation of the compactor, and then withdrawing the compactor from the canal and so as to leave the plasticized gutta percha therein, and such that the gutta percha then cools and hardens to form a solid filler in the canal.

8. The method as defined in claim 7 wherein said elongate shank portion terminates in a pilot end, with at least one helical flute formed in said shank portion along a length of said shank portion adjacent said pilot end, and with a helical land at the periphery of the shank portion and extending between axially adjacent flute segments.

9. The method as defined in claim 8 wherein the width of said helical land is at least about 15% of the pitch of said at least one helical flute.

10. The method as defined in claim 9 wherein said helical land lies along an arc of a circle when viewed in transverse cross section.

11. The method as defined in claim 10 wherein said compactor further comprises a coupling mounted at the end opposite said pilot end for releasably connecting the compactor to the chuck of a machine driven handpiece.

12. An endodontic compactor comprising a shank portion terminating at a pilot end and including a working length adjacent said pilot end, coupling means mounted to said shank portion at the end thereof opposite said pilot end for releasably connecting the compactor to the chuck of a machine driven handpiece, at least one continuous helical flute of left-handed orientation formed in said working length of said shank portion and so as to form a helical land at the periphery of said working length and extending axially between adjacent flute segments, with the width of said helical land being at least about 15% of the pitch of said at least one helical flute and with said helical land lying along an arc of a circle when viewed in transverse cross section and a coating of alpha phase gutta percha overlying said working length of said shank portion.

13. The endodontic instrument as defined in claim 12 wherein said working length is tapered toward said pilot end at an included angle of between about ½ and 4 degrees.

* * * * *

UNITED STATES PATENT AND TRADEMARK OFFICE
CERTIFICATE OF CORRECTION

PATENT NO.    :   5,302,129
DATED         :   April 12, 1994
INVENTOR(S)   :   Heath et al.

It is certified that error appears in the above-identified patent and that said Letters Patent is hereby corrected as shown below:

Column 5, line 18, "0.0004" should be --0.004--.

Column 6, line 26, "rotting" should be --rotating--.

Column 6, line 41, "with" should be --the--.

Column 6, line 50, "chunk" should be --chuck--.

Column 7, line 2, "mod" should be --mold--.

Signed and Sealed this

Tenth Day of January, 1995

Attest:

BRUCE LEHMAN

*Attesting Officer*           *Commissioner of Patents and Trademarks*